United States Patent
Vancaillie et al.

(10) Patent No.: US 11,273,164 B2
(45) Date of Patent: Mar. 15, 2022

(54) COMPOSITIONS FOR THE TREATMENT OF CHRONIC VULVAL AND PERINEAL PAIN AND SYMPTOMS AND CONDITIONS ASSOCIATED THEREWITH

(71) Applicant: TA Pharma Pty Limited, Castlecrag (AU)

(72) Inventors: Thierry Vancaillie, Castlecrag (AU); Alan Hewitt, Wrexham (GB)

(73) Assignee: TA Pharma Pty Limited, Castlecrag (AU)

( * ) Notice: Subject to any disclaimer, the term of this patent is extended or adjusted under 35 U.S.C. 154(b) by 0 days.

(21) Appl. No.: 16/098,428

(22) PCT Filed: May 1, 2017

(86) PCT No.: PCT/AU2017/050398
§ 371 (c)(1),
(2) Date: Nov. 1, 2018

(87) PCT Pub. No.: WO2017/190183
PCT Pub. Date: Nov. 9, 2017

(65) Prior Publication Data
US 2019/0099432 A1 Apr. 4, 2019

(30) Foreign Application Priority Data
May 2, 2016 (AU) .................. 2016901605

(51) Int. Cl.
| | |
|---|---|
| *A61K 31/565* | (2006.01) |
| *A61K 9/00* | (2006.01) |
| *A61K 9/06* | (2006.01) |
| *A61K 31/135* | (2006.01) |
| *A61K 31/55* | (2006.01) |
| *A61K 47/24* | (2006.01) |
| *A61K 47/32* | (2006.01) |
| *A61K 31/566* | (2006.01) |
| *A61K 47/14* | (2017.01) |
| *A61K 31/567* | (2006.01) |
| *A61K 47/18* | (2017.01) |
| *A61K 45/06* | (2006.01) |
| *A61K 9/107* | (2006.01) |
| *A61K 47/34* | (2017.01) |
| *A61K 47/46* | (2006.01) |

(52) U.S. Cl.
CPC .......... *A61K 31/565* (2013.01); *A61K 9/0014* (2013.01); *A61K 9/06* (2013.01); *A61K 9/107* (2013.01); *A61K 31/135* (2013.01); *A61K 31/55* (2013.01); *A61K 31/566* (2013.01); *A61K 31/567* (2013.01); *A61K 45/06* (2013.01); *A61K 47/14* (2013.01); *A61K 47/183* (2013.01); *A61K 47/24* (2013.01); *A61K 47/32* (2013.01); *A61K 47/34* (2013.01); *A61K 47/46* (2013.01)

(58) Field of Classification Search
CPC ............... A61K 31/135; A61K 31/565; A61K 2300/00; A61K 9/06
See application file for complete search history.

(56) References Cited

U.S. PATENT DOCUMENTS

| | | | | |
|---|---|---|---|---|
| 5,837,289 A | * | 11/1998 | Grasela | A61K 9/0014 424/484 |
| 2002/0099003 A1 | * | 7/2002 | Wilson | A61K 9/0034 514/573 |
| 2004/0044080 A1 | * | 3/2004 | Place | A61K 9/0034 514/573 |
| 2004/0198706 A1 | * | 10/2004 | Carrara | A61K 9/0014 514/169 |
| 2007/0292461 A1 | | 12/2007 | Tamarkin et al. | |
| 2016/0051683 A1 | | 2/2016 | Banov | |

FOREIGN PATENT DOCUMENTS

| | | |
|---|---|---|
| WO | WO9745125 | * 12/1997 |
| WO | WO-2007/021805 | 2/2007 |
| WO | WO-2010/118461 | 10/2010 |
| WO | WO2014018563 | * 1/2014 |

OTHER PUBLICATIONS

Lotery et al., Vulvodynia. The Lancet, 363, pp. 1058-1060 (Year: 2004).*
Gardella et al., Effect of local estrogen therapy (LET) on urinary and sexual symptoms in premenopausal eomen with interstitial cystitis/bladder pain syndrome (IC/BPS), Gynecological Endocrinology, vol. 31(10), English Abstract (Year: 2015).*
Head, Estriol: Safety and Efficacy, Alternative Medicine Review, vol. 3(2), pp. 101-113 (Year: 1998).*
Pandey et al., Pluronic lecithin organogel as a topical drug deliver system. Drug Delivery, vol. 17(1), pp. 38-47, (Year: 2010).*
Sahoo et al., Organogels: Properties and Applications in Drug Delivery. Designed Monomers and Polymers, vol. 14, pp. 95-108, (Year: 2011).*
Belgamwar et al., Pluronic lecithin organogel. Asian J. of Pharmaceutics, p. 134-138, Jul.-Sep. 2008.*

(Continued)

*Primary Examiner* — Barbara P Badio
(74) *Attorney, Agent, or Firm* — Morrison & Foerster LLP

(57) ABSTRACT

Provides herein are compositions for the treatment of chronic vulval or perineal pain, and of symptoms or conditions associated therewith, comprising an estrogen, optionally estriol, and a tricyclic antidepressant, optionally amitriptyline, formulated for topical, transdermal or transmucosal administration. Also provided are methods for the production of said compositions and to uses thereof in the treatment of chronic vulval or perineal pain, and of symptoms or conditions associated therewith.

11 Claims, No Drawings

(56) References Cited

OTHER PUBLICATIONS

Cox et al., "Assessment and management options for women with vulvodynia", Journal of Midwifery & Women's Health (2012) 57(3):231-240.
Methodist Physicians Clinic, "Vulvodynia", [retrieved from internet on Jun. 27, 2017] <URL: http://www.methodistsexualwellness.com/services/vulvodynia/> published on Mar. 26, 2016.
Boardman, "Topical Therapy for Vulvodynia," NVA News (2005) vol. XI, Issue I, 12 pages.
Database Medline, accession No. NLM21846439 (2011) 2 pages.
Haefner et al., "The Vulvodynia Guideline," Journal of Lower Genital Tract Disease (2005) 9(1):40-51.
Pagano et al., "Use of Amitriptyline Cream in the Management of Entry Dyspareunia Due to Provoked Vestibulodynia," Journal of Lower Genital Tract Disease (2012) 16(4):394-397.
Shah et al., "Update in Diagnosis and Treatment of Chronic Pelvic Pain Syndromes," Curr. Bladder Dysfunct. Rep. (2015) 10(3):198-206.
Loyd et al., "The History of Pluronic Lecithin Organogel: an Interview With Marty Jones, Bspharm, FACA, FIACP," International Journal of Pharmacceutical Compounding (2003) 7(3):180-183.
Ruoss et al., "Topical treatment of vulvodynia, dyspareunia and pudendal neuralgia: A single clinic audit of amitriptyline and oestriol in organogel," Aust N Z J Obstet Gynaecol (2021) 1-5.
Perez-Lopez and Hita-Contreras, "Management of pudendal neuralgia," Climacteric (2014) 17:654-656.

\* cited by examiner

COMPOSITIONS FOR THE TREATMENT OF CHRONIC VULVAL AND PERINEAL PAIN AND SYMPTOMS AND CONDITIONS ASSOCIATED THEREWITH

TECHNICAL FIELD

The present invention relates generally to compositions and methods for the treatment of chronic vulval and perineal pain. Compositions of the invention are formulated for topical, transdermal or transmucosal delivery and comprise an estrogen, typically estriol, and a tricyclic antidepressant, typically amitriptyline.

BACKGROUND OF THE INVENTION

Vulvodynia is a complex gynecological disorder characterised by chronic pain localized to the vulva. It is a potentially debilitating condition that can last for years, cause physical disability, sexual dysfunction, and psychological difficulties. Daily activities and quality of life can be significantly impaired with many sufferers experiencing difficulty walking or sitting for long periods, sensitivity to clothing touching the vaginal area, and mild to intense pain typically described as burning, stinging or itching. Although often difficult to diagnose, it is typically estimated that in excess of 15 percent of the adult female population in western countries may experience vulvodynia at some point during their lifetime. It most commonly affects women of child bearing age.

The most common form of vulvodynia is vulvar vestibulitis. Women with vulvar vestibulitis typically experience pain involving and limited to the vestibule and only during or after touch or pressure is applied. Vulvar vestibulitis is characterized by pain, tenderness, vestibular erythema, itching, swelling and urethritis. The pain may be described as sharp, burning, or a sensation of rawness. Generalized vulvodynia is characterized by diffuse pain and/or a burning sensation on or around the vulva, the labia majora, labia minor, and/or the vestibule. The pain can be constant or intermittent and the symptoms, although not necessarily caused by touch or pressure to the vulva, can be exacerbated by physical contact to the area.

The etiology of vulvodynia is unknown. However, it has been hypothesized that viral, fungal and bacterial assaults, allergic reactions, neuropathic processes and an autoimmune response may play a role. Irritation of the muscles that support the uterus, bladder and rectum (pelvic floor muscle or levator ani myalgia) as well as irritation of the nerves of the vulval tissue, known as pudendal neuralgia, may result in additional painful symptoms associated with vulvodynia.

Pudendal neuralgia (or also known as chronic perineal pain) is a term referring to chronic pain within the distribution of the pudendal nerve, which comprises the vulva as well as the labia majora and the skin around the anus as well as part of the mons veneris. The pudendal nerve also innervates the urethra and the anal mucosa. Thus the dysfunction of the pudendal nerve extends not only to the sensory function of the perineal skin (including the vulva) but also to voiding and defecation. Symptoms such as the constant urge to void or the sensation of a foreign body in the rectum can occur. These symptoms are not classified as pain per se but nevertheless contribute to the individual's disability.

Because of the potential for multiple causes, chronic pain such as pudendal neuralgia and vulvodynia can be difficult to treat. First-line therapy typically involves the treatment of suspected causes by pharmacologic treatment of infections and the discontinued use of suspected irritants and therapeutic agents that may contribute to the problem. Oral medications such as antihistamines, and tricyclic antidepressants, oral supplements such as calcium citrate, dietary changes and physical therapy, such as pelvic floor muscle re-education, may provide some symptomatic relief. More invasive treatments include interferon intra lesional injections, laser therapy and surgery, however these options are costly and may be associated with complications such as hematoma, wound dehiscence and uneven healing. There is no known cure as such for chronic pain syndromes such as vulvodynia and pudendal neuralgia.

There remains a need for the development of cost effective, simple to use treatment options for the chronic vulval and perineal pain associated with conditions such as vulvodynia and pudendal neuralgia.

SUMMARY OF THE INVENTION

A first aspect of the present invention provides a composition for the treatment of chronic vulval or perineal pain, or of a symptom or condition associated therewith, the composition comprising an estrogen and a tricyclic antidepressant, wherein the composition is formulated for topical, transdermal or transmucosal administration.

In particular embodiments the composition is a topical composition.

The composition may, for example, be in the form of a gel, cream, ointment or lotion.

The estrogen may be a natural or synthetic estrogen. The estrogen may be selected from the group consisting of estriol, estrone, 17 beta-estradiol, estradiol, estradiol benzoate, estradiol 17 beta-cypionate, ethinyl estradiol, mestranol, moxestrol, mytatrienediol, polyestradiol phosphate, quinestradiol, quinestrol, and any combination thereof.

Typically the estrogen displays weak estrogenic activity. In particular embodiments the weak estrogen is estriol.

The tricyclic antidepressant may be selected from amitriptyline, nortriptyline and desipramine. In particular embodiments the tricyclic antidepressant is amitriptyline. The amitriptyline may be in the form of amitriptyline hydrochloride.

In exemplary embodiments the composition is a gel composition, optionally an organogel. The gel composition may be produced using as two phase system comprising an organic phase and an aqueous phase. In one embodiment the organic phase comprises a mixture of lecithin and isopropyl palmitate. In one embodiment the aqueous phase comprises a poloxamer.

Typically the estrogen (more typically wherein the estrogen is estriol) is dissolved or dispersed in the organic phase and the tricyclic antidepressant (more typically wherein the tricyclic antidepressant is amitriptyline or amitriptyline hydrochloride) is dissolved in the aqueous phase.

Optionally the composition, or at least the organic phase in a two phase gel system, further comprises a solubilizing agent.

The condition associated with chronic vulval pain may be vulvodynia. The vulvodynia may be localized or generalized vulvodynia. The condition may be selected from vulval vestibulitis, localized provoked vestibulodynia (LPV), dysesthetic vulvodynia, vulvar dermatoses, cyclic vulvovaginitis, or pelvic floor tension myalgia (levator ani myalgia). The condition associated with chronic perineal pain may be pudendal neuralgia. The symptom or associated condition may comprise urethritis, urinary frequency or urgency or faecal frequency or urgency.

A second aspect of the invention provides a method for the treatment of chronic vulval or perineal pain, or of a symptom or condition associated therewith, the method comprising topically, transdermally or transmucosally administering to a female subject in need thereof a composition comprising an estrogen and a tricyclic antidepressant.

Typically the method comprises the administration of a composition according to the first aspect.

A third aspect of the invention provides the use of an estrogen and a tricyclic antidepressant for the manufacture of a composition for the treatment of chronic vulval or perineal pain, or of a symptom or condition associated therewith, wherein the composition is formulated for topical, transdermal or transmucosal administration.

A fourth aspect of the invention provides a topical composition for the treatment of chronic vulval or perineal pain, or of a symptom or condition associated therewith, the composition comprising estriol and amitriptyline.

The composition may, for example, be in the form of a gel, cream, ointment or lotion.

In exemplary embodiments the composition is a gel composition, optionally an organogel. The gel composition may be produced using as two phase system comprising an organic phase and an aqueous phase. In one embodiment the organic phase comprises a mixture of lecithin and isopropyl palmitate. In one embodiment the aqueous phase comprises a poloxamer.

Typically the estrogen (more typically wherein the estrogen is estriol) is dissolved or dispersed in the organic phase and the tricyclic antidepressant (more typically wherein the tricyclic antidepressant is amitriptyline or amitriptyline hydrochloride) is dissolved in the aqueous phase.

Optionally the composition, or at least the organic phase in a two phase gel system, further comprises a solubilizer.

A fifth aspect of the invention provides a method for the treatment of chronic vulval or perineal pain, or of a symptom or condition associated therewith, the method comprising topically administering to a female subject a composition comprising estriol and amitriptyline.

Typically the method comprises the administration of a composition according to the fourth aspect.

A sixth aspect of the invention provides the use of estriol and amitriptyline for the manufacture of a composition for the treatment of chronic vulval or perineal pain, or of a symptom or condition associated therewith, wherein the composition is formulated for topical administration.

DETAILED DESCRIPTION OF THE INVENTION

In the context of the present specification, the terms "a" and "an" are used herein to refer to one or to more than one (i.e. to at least one) of the grammatical object of the article. By way of example, "an element" means one element or more than one element.

In the context of the present specification, the term "comprising" means "including principally but not necessarily solely". Furthermore, variations of the word "comprising", such as "comprise" and "comprises", have correspondingly varied meanings.

In the context of the present specification, the term "about" is understood to refer to a range of values that a person of skill in the art would consider equivalent to the recited value in the context of achieving the same function or result.

The term "associated with" as used in the context of a condition associated with chronic vulval pain means a condition that may have as an underlying cause chronic vulval pain, or that may otherwise be associated, either directly or indirectly, with chronic vulval pain.

The term "weak estrogenic activity" as used herein means that, compared to a more potent estrogenic compound such as 17β-estradiol, the compound displaying weak estrogenic activity does not stimulate the nuclear receptor effectively. For example, estriol is an agonist as well as an antagonist of the beta estrogen receptor, and prevents binding of estradiol, the more potent human estrogen, to the G protein-coupled estrogen receptor. For use in accordance with the present invention, compounds with weak estrogenic activity, will typically have a stimulatory effect on the mucosa without significant effect on the nucleus, therefore only minimally stimulating the estrogen receptor positive cells elsewhere in the body, namely breast and uterus. Thus, compounds with weak estrogen activity, such as estriol, may have less unwanted systemic effects and more pronounced, advantageous local effects than a more potent estrogen, making them particularly suitable components of compositions of the present invention.

As used herein the terms "treating" and "treatment" refer to any and all uses which remedy a condition or one or more symptoms, or otherwise hinder, retard, or reverse the progression of a condition or one or more symptoms thereof in any way whatsoever. Thus the terms "treating" and the like are to be considered in their broadest context. For example, treatment does not necessarily imply that a patient is treated until total recovery.

The present invention provides compositions and methods for treating chronic vulval and perineal pain, and symptoms and conditions associated with such pain. More particularly, provided herein are compositions comprising an estrogen and a tricyclic antidepressant, wherein the composition is formulated for topical, transdermal or transmucosal administration. Also provided herein are methods of treatment of pain and associated symptoms and conditions as described herein, employing combinations of an estrogen and a tricyclic antidepressant, by topical, transdermal or transmucosal administration.

Methods and compositions of the invention are applicable the treatment of a variety of conditions and symptoms associated with chronic vulval and perineal pain including, but not limited to, vulvodynia, pudendal neuralgia, pelvic floor tension myalgia, the constant urge to void, or the sensation of a foreign body in the rectum, urethritis, and the pain associated with any of these conditions or symptoms. The vulvodynia may be localized or generalized vulvodynia. The condition may be selected from, for example, vulval vestibulitis, localized provoked vestibulodynia (LPV), dysesthetic vulvodynia, vulvar dermatoses or cyclic vulvovaginitis.

The estrogen present in the composition may be a natural or synthetic estrogen. The estrogen may be selected, for example, from the group consisting of estriol, estrone, 17 beta-estradiol, estradiol, estradiol benzoate, estradiol 17 beta-cypionate, ethinyl estradiol, mestranol, moxestrol, mytatrienediol, polyestradiol phosphate, quinestradiol, quinestrol, and any combination thereof. Typically the estrogen will display weak estrogenic activity. Accordingly, in particular exemplary embodiments of the invention the estrogen is estriol. Those skilled in the art will appreciate that other active compounds having estrogenic activity, typically weak estrogenic activity, may be used as an alternative or in addition. Estriol is a so-called weak estrogen which is predominantly produced during pregnancy by the placenta and the fetal liver. Estriol is an agonist as well as an antagonist of the beta estrogen receptor, and prevents binding of estradiol, the more potent human estrogen, to the G protein-coupled estrogen receptor. Estriol has an excellent stimulatory effect on mucosal tissue, without significant effect on the nucleus. Thus, the use of estriol is associated with less unwanted systemic effects and enhanced beneficial local effects than a more potent estrogen.

The tricyclic antidepressant present in the composition may be selected, for example, from the group consisting of amitriptyline, nortriptyline and desipramine. In particular exemplary embodiments of the invention the tricyclic antidepressant is amitriptyline. The amitriptyline may be in any form suitable for topical, transmucosal or transdermal administration, such as amitriptyline hydrochloride. Those skilled in the art will appreciate that other tricyclic antidepressants may be used as an alternative or in addition. The amitriptyline (or equivalent) acts as a topical anaesthetic when applied directly to a tegument (skin, mucosa), reducing the sensitivity of the tegument to touch. This is a pharmacological effect different from that obtained when the molecule is introduced via the gastro-intestinal tract.

The estrogen and the tricyclic antidepressant may each be present in the composition in an amount between about 0.0005% (w/w) and about 20% (w/w), between about 0.0005% (w/w) and about 10% (w/w), between about 0.005% (w/w) and about 5% (w/w), between about 0.005% (w/w) and about 3% (w/w), between about 0.005% (w/w) and about 1% (w/w), or between about 0.005% (w/w) and about 0.5% (w/w).

In embodiments in which the tricyclic antidepressant is amitriptyline, the amitriptyline may be present at about, for example, 0.05% (w/w), 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2% (w/w), 2.1% (w/w), 2.2% (w/w), 2.3% (w/w), 2.4% (w/w), 2.5% (w/w), 2.6% (w/w), 2.7% (w/w), 2.8% (w/w), 2.9% (w/w), 3% (w/w), 3.2% (w/w), 3.4% (w/w), 3.6%, 3.8% (w/w) or 4% (w/w). The skilled addressee will appreciate that the amount of amitriptyline (or other tricyclic antidepressant) may be varied depending on a variety of factors including, for example, the subject to be treated (such as age, other conditions suffered, general health and wellbeing) and the nature and severity of the pain or condition to be treated. Such variations are well within the skill of the ordinary person skilled in the art and may be made without undue burden.

In embodiments in which the estrogen is estriol, the estriol may be present at about, for example, 0.01% (w/w), 0.02% (w/w), 0.03% (w/w), 0.04% (w/w), 0.05% (w/w), 0.06% (w/w), 0.07% (w/w), 0.08% (w/w), 0.09% (w/w), 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1% (w/w), 1.2% (w/w), 1.4% (w/w), 1.6% (w/w), 1.8% (w/w), or 2% (w/w). Alternatively, the estriol may be present at, for example, between about 100 µg/gm and about 500 µg/gm based on the weight of the composition. For example the estriol may be present at about 100 µg/gm, 125 µg/gm, 150 µg/gm, 175 µg/gm, 200 µg/gm, 225 µg/gm, 250 µg/gm, 275 µg/gm, 300 µg/gm, 325 µg/gm, 350 µg/gm, 375 µg/gm, 400 µg/gm, 425 µg/gm, 450 µg/gm, 475 µg/gm, or 500 µg/gm based on the weight of the composition. The skilled addressee will appreciate that the amount of estriol (or other estrogen) may be varied depending on a variety of factors including, for example, the subject to be treated (such as age, other conditions suffered, general health and wellbeing) and the nature and severity of the pain or condition to be treated. Such variations are well within the skill of the ordinary person skilled in the art and may be made without undue burden.

In an exemplary embodiment, a composition of the invention comprises amitriptyline at about 0.5% (w/w) and estriol at about 300 µg/gm based on the weight of the composition.

Compositions of the invention may further comprise one or more additional agents or compounds such as anti-inflammatory agents, antioxidants, anti-erythema actives, antimicrobial agents, essential oils, herbal extracts, vitamins, and the like.

Exemplary anti-inflammatory agents that may be employed include steroidal and non-steroidal compounds such as those suitable for topical administration. Suitable steroidal compounds include clobetasol propionate, betamethasone dipropionate, halobetasol proprionate, diflorasone diacetate, fluocinonide, halcinonide, amcinonide, desoximetasone, triamcinolone acetonide, mometasone furoate, fluticasone propionate, betamethasone dipropionate, fluocinolone acetonide, hydrocortisone valerate, hydrocortisone butyrate, flurandrenolide, triamcinolone acetonide, mometasone furoate, triamcinolone acetonide, fluticasone propionate, desonide, fluocinolone acetonide, hydrocortisone valerate, prednicarbate, triamcinolone acetonide, desonide, hydrocorti-sone, hydrocortisone aceponate, hydrocortisone buteprate, methylprednisolone aceponate, mometasone furoate and prednicarbate. Suitable non-steroidal anti-inflammatory compounds include indomethacin, ketoprofen, felbinac, diclofenac, ibuprofen, piroxicam, benzydamin, acetylsalicylic acid, diflunisal, salsalate, naproxen, fenoprofen, ketoprofen, flurbiprofen, oxaprozin, loxoprofen, indomethacin, sulindac, etodolac, ketorolac, diclofenac, nabumetone, piroxicam, meloxicam, tenoxicam, droxicam, lornoxicam, isoxicam, mefenamic acid, meclofenamic acid, flufenamic acid, tolfenamic acid, firocoxib, and licofelone, semi-synthetic glycosaminoglycosan ethers, flavanols, flavonoids, isoflavones and derivatives. Other suitable anti-inflammatories include, for example, zinc cream or lotion, and vitamin E oil, cream or lotion.

Examples of antioxidants include, but are not limited to, water-soluble antioxidants such as sulfhydryl compounds and their derivatives (for example sodium metabisulfite and N-acetyl-cysteine), lipoic acid and dihydrolipoic acid, resveratrol and lactoferrin. Oil-soluble antioxidants include, but are not limited to butylated hydroxytoluene, retinoids, tocopherols, carotenoids, ubiquinone, dimethylmethoxychromanol and isoquercetin.

Examples of anti-erythema actives include, but are not limited to *Matricaria recutita* extract, *Anthemis nobilis* extract, *Centella asiatica* extract, *Crithmum maritimum* extract, *Gingko biloba* extract, *Centaurea cyaneus* extract, and extracts from *Euphrasia* species.

Exemplary antimicrobial agents include anti-bacterial, anti-viral, anti-fungal and anti-protozoal compounds. Examples of anti-bacterial compounds include, but are not limited to antibiotics such as erythromycin, spiramycin, clarithromycin, clindamycin and tretinoin. Examples of anti-viral compounds include, but are not limited to acyclovir, amantadine, valacyclovir and rimantadine. Examples of anti-fungal compounds include, but are not limited to chlorphenesin, clioquinol, haloprogin, undecylenic acid, tolnaftate, fluconazole, butoconazole, clotrimazole, econazole, miconazole, terconazole and tioconazole. Examples of antiprotozoal compounds include, but are not limited to antimalarial drugs, spiramycin and clioquinol.

Essential oils may enhance the emollient and penetration properties of the composition. Exemplary essential oils include, but are not limited to lemongrass oil, tea tree oil, thyme oil, and lavender oil.

Suitable vitamins include but are not limited to vitamin A, pro vitamin A, vitamin $B_1$, vitamin $B_2$, vitamin $B_3$, vitamin $B_4$, vitamin $B_5$, vitamin $B_6$, vitamin $B_{12}$, vitamin D, vitamin $D_2$, vitamin $D_3$, tocopherol (vitamin E), vitamin F and vitamin Ki.

The compositions may comprise one or more pharmaceutically acceptable humectants, emollients or preservatives. The inclusion of humectants and emollients provide a moisturising effect to the topical compositions when applied repeatedly to the skin thereby minimising any drying effect that the composition may impart when applied to sensitive membranes such as around the vagina.

A wide variety of suitable emollients are known to those skilled in the art. See for example the *International Cosmetic Ingredient Dictionary and Handbook*, Eds. Wenninger and McEwen, The Cosmetic, Toiletry, and Fragrance Assoc., Washington, D.C., 7th Edition, 1997. Emollients useful in the present invention include, but are not limited to: glycerin, propylene glycol, sorbitol, sorbitan palmitate, lanolin, lanolin derivatives, polyethylene glycol (for example PEG300), aloe vera, glucamate DOE 120, allantoin, alginates, monoester salts of sulfosuccinates, ceramides, and mixtures thereof. Further exemplary moisturisers include, but are not limited to, cetyl palmitate, castor oil, jojoba seed oil, grape seed oil, sunflower seed oil, safflower seed oil, diglycerin, oleic acid, dimethicone copolyol, dextrin, jojoba esters, panthenol, squalene, coconut oil, cocoa butter, honey, hydrogenated lecithin, isopropyl isostearate, hydrogenated vegetable oil, glyceryl distearate, marine exopolysaccharides, polyfructol, hyaluronic acid, hydrolysed hyaluronic acid, flavonoids from *Salvia sclarea* and *Citrus aurantiaca*, erythritol, seed extract from *Tamarindus indica*, and *Opuntia ficus-indica* extract.

Examples of humectants include, but are not limited to glycerol, sorbitol, polyethylene glycol, mono- and oligomeric sugars, natural extracts such as *quillaia*, lactic acid and urea.

Examples of preservatives include but are not limited to benzyl alcohol and parabens.

Compositions of the invention may be formulated for topical, transdermal or transmucosal administration. Typically the compositions are formulated for topical administration. Suitable pharmaceutically acceptable carriers, diluents, excipients and adjuvants suitable for topical compositions include demineralised or distilled water; saline solution; vegetable based oils such as peanut oil, safflower oil, olive oil, cottonseed oil, maize oil, sesame oil, *Arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Compositions of the invention may be in any form suitable for topical, transdermal or transmucosal administration. For example, the composition may be in the form of a cream, ointment, lotion, gel, paste, solution, spray or the like. Compositions may prepared so as to contain liposomes, micelles, and/or microspheres.

Ointments, as is well known in the art, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. Suitable ointment bases are typically grouped into four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Water-soluble ointment bases are prepared from polyethylene glycols of varying molecular weight.

Creams, as also well known in the art, are viscous liquids or semisolid emulsions, either oil-in-water or water-in-oil. Cream bases are typically water-washable, and contain an oil phase, an emulsifier and an aqueous phase. The oil phase may be comprised of petrolatum and a fatty alcohol such as cetyl or stearyl alcohol. The aqueous phase may exceed the oil phase in volume, and generally contains a humectant. The emulsifier in a cream formulation is generally a nonionic, anionic, cationic or amphoteric surfactant.

Methods for the preparation of suitable ointments and creams are well known to those skilled in the art, as are methods for the preparation of lotions, gels, pastes, solutions, sprays and the like, for example with reference to any one of numerous texts well known in the field (such as Remington: The Science and Practice of Pharmacy).

In particular embodiments, the composition may be in the form of a water-based gel wherein the gel includes at least one gelling agent, a solubilising agent and water.

Gelling agents that may be used in the compositions of the invention include, but are not limited to: algal extracts, gums, polysaccharides, starches, pectins, hydrolysed proteins, cellulose derivatives and polymers comprising pendant carboxylic acid groups, or esters thereof, polymers comprising pendant anhydrides of dicarboxylic acid groups and block co-polymers, including poloxomers, based on ethylene oxide and/or propylene oxide.

Algal extracts that may be used include, but are not limited to alginates and carrageenans. Cellulose derivatives that may be used include, but are not limited to methylcelluloses, ethylcelluloses hydroxypropylmethylcelluloses, hydroxyethylcelluloses and carboxymethylcelluloses, which may or may not be cross-linked. Hydrolysed proteins include but are not limited to gelatin.

Polymers comprising pendant carboxylic acid groups may be homopolymers, copolymers or interpolymers comprising an acrylic acid backbone, for example carbomers. In one embodiment, the gelling agent is a polymer of acrylic acid cross-linked with polyalkenyl ethers or divinyl glycol. In an alternative embodiment, the gelling agent is a copolymer of acrylic acid and long-chain alkyl acrylates crosslinked with polyalkenyl ethers, for example allyl pentaerythritol.

Carbomers suitable for use in the present invention include, but are not limited to, high molecular weight crosslinked polyacrylic acid polymers commercially available under the trade names CARBOPOL® (Lubrizol Advanced Materials, Inc.), PEMULEN® (Lubrizol Advanced Materials, Inc.,), NOVEON® (Lubrizol Advanced Materials, Inc.), and SYNTHALEN® (3V Sigma), and the carboxyl vinyl polymer HIVIS WAKO® (Wako Pure Chemicals Co.). Carbomers used in the present invention may be carbomers having Brookfield viscosities in the range of about 40,000 to 70,000 mPa·s at 25° C. In one embodiment, the carbomer may be CARBOPOL® 980.

Block co-polymers based on ethylene oxide and/or propylene oxide that are suitable for use in the present invention include those commercially available under the trade name PLURONIC®.

The amount of gelling agent present in the composition will depend on the particular gelling agent being used. Typically the amount of gelling agent present in the composition is between about between about 0.01% (w/w) and about 50% (w/w), or between about 0.05% (w/w) and about 40% (w/w), or between about 0.05% (w/w) and about 30% (w/w), or between about 0.05% (w/w) and about 20% (w/w), or between about 0.05% (w/w) and about 10% (w/w), or between about 0.05% (w/w) and about 5% (w/w), or between about 0.05% (w/w) and about 3% (w/w), or between about 0.1% (w/w) and about 2% (w/w). Where a gelling agent sold under the trade name CARBOPOL® is employed, the amount used may be in the range of between about 0.05% (w/w) and about 5% (w/w). Where a gelling agent sold under the trade name PLURONIC® is employed, the amount used may be in the range of between about 1% (w/w) and about 30% (w/w).

In exemplary embodiments the composition is a gel composition, optionally an organogel. The gel composition may be produced using as two phase system comprising an organic phase and an aqueous phase. Typically, as will be understood by those skilled in the art, blending or mixing of the organic phase and the aqueous phase until high shear may be required to produce the organogel. The ratio of the organic phase to the aqueous phase may be between about 1:5 and about 5:1, such as about 1:5, 1:4, 1:3, 1:2, 1:1, 2:1, 3:1, 4:1 or 5:1. In an exemplary embodiment the ratio of the organic phase and the aqueous phase may be about 1:2.

In one embodiment the organic phase comprises a mixture of lecithin and isopropyl palmitate. The ratio of the lecithin to isopropyl palmitate in the organic phase may be between about 1:5 and 5:1, between 1:4 and 4:1, between 1:3 to 3:1, between 1:2 and 2:1, or about 1:1. In one embodiment the aqueous phase comprises a poloxamer, such as, for example PLURONIC® F-127. Those skilled in the art will appreciate that a range of other poloxamers may be used without departing from the scope of the invention. The appropriate constituents of the organic phase and the aqueous phase can be determined by those skilled in the art without experimentation.

Thus, an exemplary two phase system is the PLURONIC® Lecithin Organogel (PLO) system.

In an exemplary embodiment the estriol is typically first dissolved (either fully dissolved or at least partially dissolved) or dispersed in a suitable solvent, such as propylene glycol prior to the addition of the organic phase such as the lecithin/isopropyl palmitate mixture. The ratio of propylene glycol to the lecithin/isopropyl palmitate mixture may be between about 1:10 and about 10:1, such as about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1. In an exemplary embodiment, the ratio of propylene glycol to the lecithin/isopropyl palmitate mixture may be about 4:10.

In such two phase systems, typically the estrogen (more typically wherein the estrogen is estriol) is dissolved or dispersed in the organic phase and the tricyclic antidepressant (more typically wherein the tricyclic antidepressant is amitriptyline or amitriptyline hydrochloride) is dissolved in the aqueous phase.

Accordingly, also provided herein is a method for producing a composition comprising an estrogen and a tricyclic antidepressant, optionally estriol and amitriptyline, comprising: incorporating the estrogen, optionally estriol, in an organic phase, wherein the organic phase optionally comprises a mixture of lecithin and isopropyl palmitate; incorporating the tricyclic antidepressant, optionally amitriptyline, in an aqueous phase, wherein the aqueous phase optionally comprises a poloxamer such as a Pluronic® poloxamer, and mixing the organic phase and the aqueous phase, optionally under conditions of high shear, to produce a gel composition.

Optionally the composition, or at least the organic phase in a two phase gel system, further comprises a solubilizing agent.

The solubilising agent may be selected from the group consisting of: pyrrolidone or a derivative thereof, castor oil, polyethoxylated castor oil, diethylene glycol monoethyl ether, propylene glycol caprylate, propylene glycol mono caprylate, medium chain glycerides, 2-methacryloxyethylphosphonylcholine, cyclodextrins and derivatives thereof, lecithin, polysorbates, PEG-phospholipids, phospholipids, cholesterol-PEG, saturated polyglycolised $C_8$-$C_{10}$ glycerides. In one exemplary embodiment, the solubilising agent is a non-alcoholic solubilising agent, for example pyrrolidone or a derivative thereof. As used herein, a non-alcoholic solubilising agent means an agent which is free or substantially free of alcohols, including polyhydric alcohols. "Substantially free" will be understood to mean less than about 0.01%, or less than about 0.005%, or less than about 0.001% of the recited component. In another exemplary embodiment the solubilising agent is diethylene glycol monoethyl ether.

The solubilising agent may be present in an amount between about 1% (w/w) and about 30% (w/w), or between about 1% (w/w) and about 20% (w/w), or between about 1% (w/w) and about 15% (w/w), or between about 1% (w/w) and about 10% (w/w). Those skilled in the art will, by routine trial and experimentation, be able to determine the amount of solubilising agent required to either dissolve or substantially solubilise the active agents.

The compositions may comprise water in an amount between about 50% (w/w) and about 90% (w/w), or between about 60% (w/w) and about 80% (w/w).

It will be appreciated by persons skilled in the art that numerous variations and/or modifications may be made to the invention without departing from the spirit or scope of the invention as broadly described. The present embodiments are, therefore, to be considered in all respects as illustrative and not restrictive.

The invention will now be described in more detail, by way of illustration only, with respect to the following examples. The examples are intended to serve to illustrate this invention and should not be construed as limiting the generality of the disclosure of the description throughout this specification.

EXAMPLES

Example 1—Exemplary Compositions Comprising Estriol and Amitriptyline

An exemplary composition contains the following ingredients:
Amitriptyline
Estriol
Ethylhexyl stearate
Emulsifying wax
Tocopheryl acetate
Aloe barbadensis leaf juice
Disodium EDTA
Sorbitol
Cyclopentasiloxane
Methylchloroisothiazolinone (and) Methylisothiazolinone
Water The amitriptyline and estriol may be provided in the form of powders, mixed with a base formulation comprising the remaining ingredients.

Example 2—Preparation of a High Bioavailability Gel Composition Comprising Estriol and Amitriptyline Estriol is essentially insoluble in water (27 mg per litre), slightly soluble in alcohol (10 mg/ml in ethanol) and soluble in pyridine (50 mg/ml). Amitriptyline HCL is soluble in water but the solubility decreases as pH increases (0.9 mg/ml at pH 6.8, and 1000 mg/ml at pH 1.2).

In an effort to produce a gel composition comprising estriol and amitriptyline the inventors selected a CARBOPOL® polymer as the gelling agent. Estriol was dissolved in an alcohol/solubiliser mix (comprising n-butanol, iso propanol, propylene glycol and diethylene glycol monoethyl ether) sufficient to hold the estriol in an aqueous solution (first solution) before adding CARBOPOL® 980. The second solution contained amitriptyline HCL in a weak phosphate buffer to control the pH at 5.7. Both solutions were prepared successfully however when mixed, no gel formed. Gel formation of the Carbomer range is affected by salt content and CARBOPOL® Ultrez 21 is more resistant to salt than CARBOPOL® 980. However this substitution did not result in gel formation. Finally the phosphate buffer was removed to reduce the salt content and triethanolamine was used to neutralise, but this also did not result in gel formation.

PLURONIC® F-127 is a difunctional block copolymer surfactant terminating in primary hydroxyl groups. At higher concentrations (20%+) it is very fluid at low temperatures (about 5° C.) but when warmed to about 30° C., becomes a non fluid clear gel. As it was determined that amitriptyline reduces the gelling properties of PLURONIC® F-127, it was decided that a two phase organic/aqueous gel system was appropriate, specifically a pluronic lecithin organogel (PLO) system. The PLO system uses PLURONIC®solution as the aqueous phase and a lecithin/isopropyl palmitate (LIP; in a 1:1 ratio) as the organic phase. These two phases, when blended under relatively high shear, produce an organogel.

For the organic phase, estriol was dissolved/dispersed (did not produce a clear solution) in propylene glycol then mixed with LIP. The ratio of propylene glycol to LIP was 4:10. For the aqueous phase, amitriptyline HCL was dissolved in water, then PLURONIC® F-127 was added to give a 20% PLURONIC®solution. The two phases were mixed using a syringe to syringe transfer method which produce a relatively high shear mixing. The ratio of organic to aqueous phases was 1:2. This produced a stable organogel with final concentrations of 300 mcg/g estriol and 0.5% w/w amitriptyline. Stability may be increased by the addition of potassium sorbate.

To increase the dissolution of the estriol in the organic phase, and thereby improve bioavailability, a combination of solubiliser (diethylene glycol monoethyl ether) and propylene glycol was employed. A 50/50 mix of diethylene glycol monoethyl ether and propylene glycol resulted in complete dissolution of the estriol. This was then blended with the LIP to produce the organic phase. Mixing the organic phase with the aqueous phase again resulted in a stable organogel.

The invention claimed is:

1. A method for the treatment of chronic vulval or perineal pain or a condition associated therewith, the method comprising topically, transdermally or transmucosally administering to a female subject in need thereof an organogel composition comprising estriol and a compound selected from amitriptyline and nortriptyline wherein the condition associated with the chronic vulval or perineal pain is selected from vulvodynia, pudendal neuralgia, and pelvic floor tension myalgia (levator ani myalgia).

2. A method according to claim 1, wherein the chronic vulval or perineal pain is associated with urinary frequency or urgency, or faecal frequency or urgency.

3. A method according to claim 1, wherein the composition is a topical composition.

4. A method according to claim 1, wherein the organogel comprises estriol and amitriptyline.

5. A method for the treatment of chronic vulval or perineal pain or a condition associated therewith, the method comprising topically, transdermally or transmucosally administering to a female subject in need thereof an organogel composition comprising estriol and amitriptyline, wherein the condition associated with the chronic vulval or perineal pain is selected from vulvodynia, pudendal neuralgia, and pelvic floor tension myalgia (levator ani myalgia).

6. A method according to claim 1, wherein the organogel is a lecithin organogel.

7. A method according to claim 6, wherein the lecithin organogel is a Pluronic lecithin organogel.

8. A method according to claim 5, wherein the organogel is a lecithin organogel.

9. A method according to claim 8, wherein the lecithin organogel is a Pluronic lecithin organogel.

10. A method according to claim 1, wherein the condition associated with the chronic vulval or perineal pain is selected from vulval vestibulitis, localized provoked vestibulodynia (LPV), dysesthetic vulvodynia, and urethritis.

11. A method according to claim 5, wherein the condition associated with the chronic vulval or perineal pain is selected from vulval vestibulitis, localized provoked vestibulodynia (LPV), dysesthetic vulvodynia, and urethritis.

* * * * *